United States Patent
Guilloux et al.

(10) Patent No.: US 7,629,439 B2
(45) Date of Patent: Dec. 8, 2009

(54) PEPTIDES DERIVED FROM THE PROTEIN MMP-2, AND THE USE THEREOF IN ANTITUMORAL IMMUNOTHERAPY

(75) Inventors: Yannick Guilloux, Nantes (FR); Francine Jotereau, Nantes (FR); Emmanuelle Godefroy, Nantes (FR); Elisabeth Diez, Saint Fiacre sur Maine (FR); Agnès Aubry, Nantes (FR)

(73) Assignees: INSERM (Institut National de la Sante et de la Recherche Medicale, Paris (FR); Universite de Nantes, Nantes (FR)

( * ) Notice: Subject to any disclaimer, the term of this patent is extended or adjusted under 35 U.S.C. 154(b) by 187 days.

(21) Appl. No.: 10/561,951

(22) PCT Filed: Jun. 24, 2004

(86) PCT No.: PCT/FR2004/001585

§ 371 (c)(1),
(2), (4) Date: Nov. 21, 2006

(87) PCT Pub. No.: WO2005/000342

PCT Pub. Date: Jan. 6, 2005

(65) Prior Publication Data

US 2007/0264275 A1 Nov. 15, 2007

(30) Foreign Application Priority Data

Jun. 25, 2003 (FR) .................................. 03 07659

(51) Int. Cl.
*A61K 38/04* (2006.01)

(52) U.S. Cl. ........................ 530/328; 530/327; 530/350

(58) Field of Classification Search ................. 530/327, 530/328, 350
See application file for complete search history.

(56) References Cited

U.S. PATENT DOCUMENTS 5,763,219 A * 6/1998 Keyomarsi
6,500,924 B1 * 12/2002 Brooks et al.

FOREIGN PATENT DOCUMENTS

| WO | 97/45137 | 12/1997 |
| WO | 01/80811 | 11/2001 |
| WO | 02/098351 | 12/2002 |

OTHER PUBLICATIONS

Elgert et al (Immunology: Understanding the Immune System, 1996, pp. 143-145).*
Brooks, Peter C. et al., "Disruption of angiogenesis by PEX, a noncatalytic metalloproteinase fragment with integrin binding activity", Cell, Cell Press, vol. 92, pp. 391-400, 1998.
Massova, Irina et al, "Matrix metalloproteinases: structures, evolution, and diversification", FASEB Journal, vol. 12, pp. 1075-1095, , 1998.
Egeblad, Mikala et al., "New functions for the matrix metalloproteinases in cancer progression", Nature Reviews Cancer, vol. 2, No. 3, pp. 161-174, 2002.

* cited by examiner

*Primary Examiner*—Stephen L Rawlings
*Assistant Examiner*—Brad Duffy
(74) *Attorney, Agent, or Firm*—Oblon, Spivak, McClelland, Maier & Neustadt, L.L.P.

(57) ABSTRACT

Peptides derived from MMP-2 metalloproteinase that form T cell epitopes when presented by MHC Class I molecules. Anti-tumor therapy using these peptides.

3 Claims, 4 Drawing Sheets

SEQUENCE LISTING

```
<160> NUMBER OF SEQ ID NOS: 4

<210> SEQ ID NO 1
<211> LENGTH: 9
<212> TYPE: PRT
<213> ORGANISM: Homo sapiens

<400> SEQUENCE: 1

Gly Leu Pro Pro Asp Val Gln Arg Val
1               5

<210> SEQ ID NO 2
<211> LENGTH: 10
<212> TYPE: PRT
<213> ORGANISM: Homo sapiens

<400> SEQUENCE: 2

Leu Gly Leu Pro Pro Asp Val Gln Arg Val
1               5                   10

<210> SEQ ID NO 3
<211> LENGTH: 8
<212> TYPE: PRT
<213> ORGANISM: Homo sapiens

<400> SEQUENCE: 3

Leu Pro Pro Asp Val Gln Arg Val
1               5

<210> SEQ ID NO 4
<211> LENGTH: 8
<212> TYPE: PRT
<213> ORGANISM: Homo sapiens

<400> SEQUENCE: 4

Gly Leu Pro Pro Asp Val Gln Arg
1               5
```

PEPTIDES DERIVED FROM THE PROTEIN MMP-2, AND THE USE THEREOF IN ANTITUMORAL IMMUNOTHERAPY

The present invention relates to peptides derived from the MMP-2 protein and to the use thereof in antitumor immunotherapy.

Peptide immunization or immunotherapy is a therapeutic approach that is currently the subject of great interest in the context of the prevention or treatment of cancers. The principle thereof is based on the induction of an immune response with respect to peptides representing T epitopes of tumor antigens recognized by cytotoxic T lymphocytes (CTLs), which play a major role in eliminating cancer cells expressing these antigens at their surface.

It will be recalled that CTLs do not recognize whole protein antigens, but peptide fragments thereof, presented by the major histocompatibility complex (MHC) molecules expressed at the surface of various cells. It is these peptide fragments that constitute the T epitopes.

The epitopes presented by the class I major histocompatibility complex (MHC I) generally have 8 to 11 amino acids, and are recognized by CD8+ T cells, which represent the major component of the cytotoxic response. The epitopes presented by the class II major histocompatibility complex (MHC II) generally have 13 to 18 amino acids and are recognized by CD4+ T cells.

The identification of these epitopes, and in particular those presented by MHC I (given the essential role of the CD8+ response in cytotoxicity), therefore constitutes an essential step for the development of antitumor immunotherapy compositions.

Melanoma is a malignant skin tumor which develops at the expense of epidermal melanocytes, namely the pigmentary cells of the skin. In France, 9 to 10 new cases per 100 000 inhabitants are currently recorded each year, i.e. close to 5000 new patients.

Two main classes of melanoma-associated antigens (MAAs) are known: the specific antigens, which are expressed very little or not at all in normal tissues, and the melanocyte differentiation antigens, which are also expressed by melanocytes (for review, see Castelli et al., 2000, *J Cell Physiol*, 182, 323-31; Kirkin et al., 2002, *Cancer Invest*, 20, 222-36).

Because of the high prevalence of melanoma-type cancers, it is desirable to identify other tumor antigens capable of inducing an antitumor cytotoxic immune response.

Matrix metalloproteases (MMPs) are Zn-dependent endopeptidases that are responsible for the degradation of various protein components of the extracellular matrix (ECM) and of basal membranes (Khasigov et al., 2001, Biochemistry, 66(2), 130-40). At the current time, 21 members of the MMP family are known in humans.

Overexpression of MMPs is observed in a large number of human cancers and it is associated with a low survival rate. In fact, MMPs have the ability to potentiate tumor progression by increasing cell growth, cell migration and angiogenesis (Egeblad and Werb, 2002, Nat. Rev. Cancer., 2(3), 161-74).

The MMP-2 protein (also called gelatinase A or collagenase type IV; OMIM 120360) cleaves collagen type IV, gelatin, and other components of the extracellular matrix. This protein is expressed in a number of normal cells and tissues; it is also overexpressed in many cancers. Numerous studies have shown that it is involved in tumor progression, metastases and angiogenesis (Liotta et al., 1980, Nature., 284 (5751), 67-8; Itoh et al., 1998, Cancer. Res., 58(5), 1048-51; Brooks et al., 1998, Cell., 92(3), 391-400).

Because of its overexpression in many tumor types, and its involvement in malignant transformation and in tumor angiogenesis, it has been proposed to use MMP-2 as a target for antitumor treatments, by inhibiting its activity (Egeblad and Werb, mentioned above; Coussens et al., 2002, Science, 295 (5564), 2387-92).

However, the MMP-2 protein was not, up until now, considered to be a target antigen capable of inducing an antitumor cytotoxic response. A fortiori, no T epitope of MMP-2 has been identified.

The inventors have now discovered that MMP-2 can be effectively processed by melanoma cells so as to generate T epitopes presented by MHC I, and inducing cytotoxic T lymphocytes capable of lysing tumor cells.

Consequently, a subject of the present invention is the use of a molecule chosen from:
- the MMP-2 metalloprotease;
- a fragment of said metalloprotease comprising a T epitope presented by MHC I;
- a polynucleotide encoding said metalloprotease or encoding said fragment;

for obtaining a medicinal product for use in antitumor immunotherapy, and more particularly for use in the treatment of melanomas expressing MMP-2.

MMP-2 fragments that can be used in accordance with the present invention encompass in particular any immunogenic peptide consisting of 8 to 11 consecutive amino acids of said metalloprotease, and constituting a T epitope presented by MHC I. These immunogenic peptides, and also the polynucleotides encoding these peptides, are also part of the subject of the present invention.

In the context of the disclosure of the present invention, the expression "T epitope presented by MHC I" is intended to mean a peptide capable of inducing a specific CTL response against the antigen from which it is derived.

By way of nonlimiting example of implementation of the present invention, the inventors have identified a peptide presented by HLA-A*0201, having the sequence (1-letter code) GLPPDVQRV (SEQ ID NO: 1).

This peptide is capable of inducing a specific CTL response with respect to HLA-A*0201 melanoma cells expressing MMP-2, and can therefore in particular be used for obtaining medicinal products for use in the treatment of HLA-A*0201 patients.

Other T epitopes in accordance with the invention can be obtained in various ways from the MMP-2 antigen.

For example, it is known that peptides capable of forming a complex with a given MHC I allele have in common the presence, at certain positions, of specific amino acid residues, called "anchor residues". Specific anchor motifs, involving amino acids called "primary anchor residues", have thus been defined for the various MHC I alleles. It has also been shown that residues located outside the primary anchor motifs (secondary anchor residues) can exert a favorable or unfavorable effect on the affinity of the peptide for the MHC.

The choice of the peptide sequences that may constitute epitopes presented by a given MHC I allele can be made, conventionally, by analysis of the peptide sequence of the MMP-2 antigen, in order to select the peptides having all or part of the primary anchor motif corresponding to this allele. Various databases listing the known anchor motifs are available: by way of examples, mention will be made of the SYF-PEITHI database (on the worldwide web at uni-tuebingen.de/uni/kxi/; Rammensee et al., Immunogenetics, 50, 213-219, 1999), or the BIMAS database (at bimas.dcrt.nih.gov/molbio/hla_bind; Parker et al., J. Immunol. 152, 163, 1994).

A subject of the present invention is also compositions comprising at least one immunogenic peptide in accordance with the invention or a polynucleotide encoding said peptide.

They may in particular be multiepitope compositions capable of generating a polyspecific CTL response, and which, for this purpose, also comprise one or more other immunogenic epitope(s). These other epitopes may be derived from MMP-2, or from one or more other antigens.

Multiepitope compositions in accordance with the invention may comprise, so as to be widely usable on a population in which the individuals carry different HLA alleles, epitopes presented by various MHC I molecules. They may also comprise, in addition, at least one epitope presented by an MHC II molecule, and capable of inducing a T-helper response.

According to a preferred embodiment of a composition in accordance with the invention, it comprises at least one chimeric polypeptide comprising one or more copies of an immunogenic peptide in accordance with the invention. In the case of a multiepitope composition, said chimeric polypeptide also comprises one or more copies of at least one other immunogenic epitope.

It is, for example, possible to inject the patient to be treated with an immunogenic peptide, or a composition in accordance with the invention as defined above, optionally combined with an appropriate adjuvant. Similarly, polynucleotides in accordance with the invention, preferably integrated into nucleic acid vectors, in particular viral vectors such as adenoviruses, can also be directly administered by injection to the patient to be treated.

The present invention also encompasses antigen-presenting cells presenting a T epitope derived from MMP-2 in accordance with the invention.

Antigen-presenting cells in accordance with the invention can be obtained from all the cells capable of presenting an antigen via MHC I. In particular, they can be obtained from professional antigen-presenting cells, for example dendritic cells.

According to a preferred embodiment of the present invention, said antigen-presenting cells are loaded in vitro, with an immunogenic peptide according to the invention, as described, for example, by Bakker et al. (Cancer Res., 55, 5330-5334, 1995) or Van Elsas et al. (Eur. J. Immunol., 26, 1683-1689, 1996).

According to another preferred embodiment of the present invention, said antigen-presenting cells are transfected, in vitro, with a polynucleotide comprising a sequence encoding an immunogenic peptide in accordance with the invention, for example a polynucleotide encoding the MMP-2 protein or encoding a fragment thereof.

The antigen-presenting cells in accordance with the invention can then be injected into a patient to be treated, as described, for example, by Kaplan et al. (J. Immunol., 163(2), 699-707, 1999) or Kim et al. (Annals of Surgical Oncology, 5(1), 64-76, 1998).

The present invention also encompasses the use of the MMP-2 protein, or of a fragment thereof, and in particular of an immunogenic peptide according to the invention, for detecting CTLs directed against MMP-2 in a biological sample obtained from an individual suffering from melanoma.

These peptides can also be used for carrying out specific sorting of these CTLs. The CTLs thus isolated can then be amplified, in vitro, and reinjected in large number (of the order of a billion) into the patient.

A subject of the present invention is thus a method of preparing CTLs directed against MMP-2, characterized in that it comprises the selection, from CTLs taken from a patient suffering from melanoma, of those that recognize the MMP-2 protein, or a fragment thereof, and in particular a peptide in accordance with the invention, and the multiplication, in vitro, of the T lymphocytes thus selected.

A subject of the present invention is also a preparation of CTLs directed against the MMP-2 protein, and in particular a preparation of CTLs that can be obtained by means of the method defined above.

The present invention also encompasses the medicinal products comprising an active ingredient chosen from:
- an immunogenic peptide in accordance with the invention;
- a multiepitope composition in accordance with the invention;
- a polynucleotide in accordance with the invention;
- an antigen-presenting cell in accordance with the invention;
- a preparation of CTLs in accordance with the invention.

The present invention will be understood more clearly from the further description which follows, which refers to nonlimiting examples illustrating the induction of an antitumor cytotoxic response by a peptide in accordance with the invention derived from the MMP-2 antigen.

EXAMPLE 1

Characterization of a CTL Clone (Clone M134.12) That Recognizes HLA-A2 Melanoma Lines CTL clones were obtained by stimulating, with autologous tumor cells (according to the protocol described by Pandolfino et al., 1992, *Eur. J. Immunol.*, 22(7), 1795-802), tumor-infiltrating lymphocytes (TILs) from a patient (HLA A*0201, B*0801, Cw*0701) suffering from melanoma. These CTL clones are capable of specifically lysing the autologous tumor cells, and of secreting TNFα and IFNγ in response to the stimulation with these cells.

One of these clones (CTL M134.12) was selected for the subsequent experiments.

The CTL clone M134.12 was cocultured in the presence of the M134 autologous line, and of various allogenic lines (M17, M113, M147, M153, M204, FM25, FM29, IPC 277/5, M25, M44, M88, M102, M117, M171, M199, M200) derived from melanomas from various HLA A*0201 patients.

After 6 hours of culture, the supernatants were removed and the TNFα concentration thereof was determined by measuring the cytotoxicity of these culture supernatants for the WEHI 164 clone 13, as described by De Plaen et al. (Methods, 12, 125-42, 1997).

Figure 1:
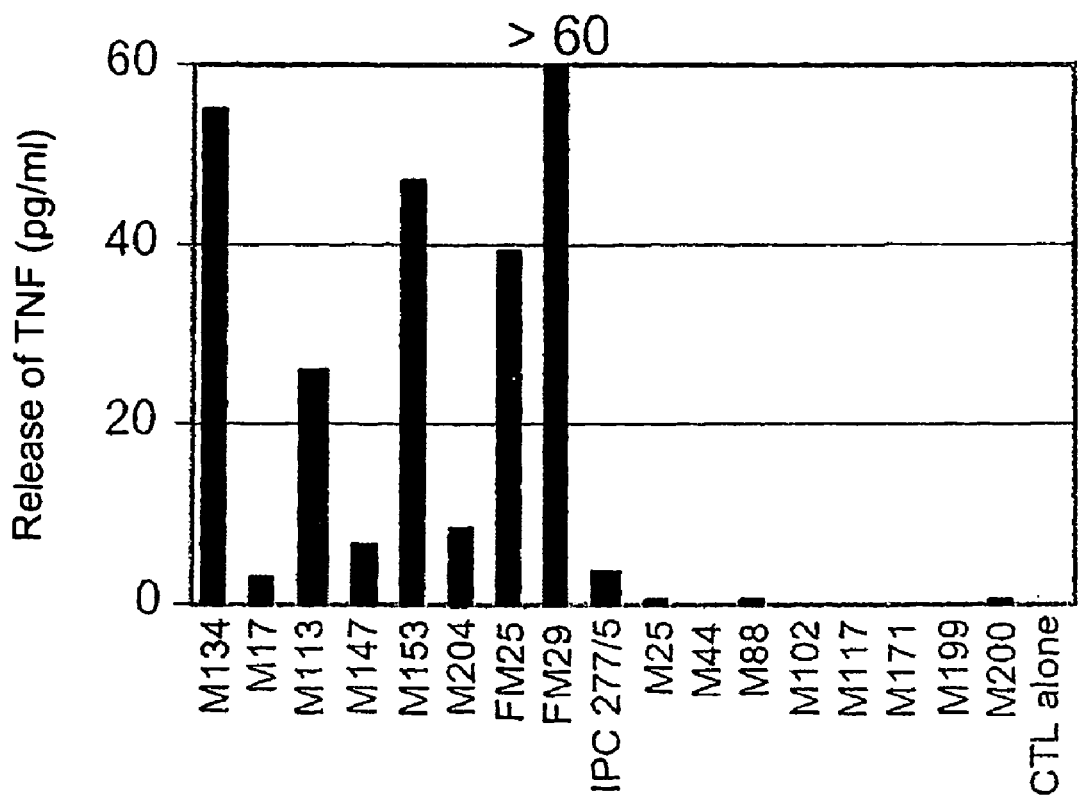
FIG. 1 graphs the concentration of TNF-α for autologous cell line M134 and various other allogenic cell lines cocultured with CTL clone M134.12.

The results are illustrated in FIG. 1.

Along the y-axis, the concentration of TNFα in pg/ml.

Along the x-axis, the various lines tested.

The CTL clone M134.12 recognizes, in addition to the M134 line, nine allogenic melanoma cell lines expressing HLA A*0201. This indicates that this CTL clone recognizes an antigen common to these lines and presented by the HLA A*0201 allele.

EXAMPLE 2

Identification of the Antigen Recognized by The CTL Clone M134.12

In order to identify the antigen recognized by the CTL clone M134.12, a cDNA library was constructed from the mRNAs of the M134 tumor cell line.

Construction of the cDNA Library

The poly-(A)⁺ mRNAs were extracted from the M134 cells using the FAST TRACK™ 2.0 kit (Invitrogen Corp., Oxon, UK). The cDNA was synthesized from the purified mRNAs using a kit (Stratagene Inc., La Jolla, Calif.). The newly synthesized cDNAs were ligated to Eco RI adapters, and then digested with Xho I and, finally, inserted at the Eco RI and Xho I sites of the eukaryotic expression vector pcDNA3.1 (Invitrogen Corp.). The recombinant plasmids obtained were electroporated into the *E. coli* strain XL1 (Stratagene Inc., La Jolla, Calif.). After electroporation, close to 60 000 ampicillin-resistant clones were isolated. In order to allow these clones to be screened, 574 groups (each of 100 ampicillin-resistant bacterial clones) were created. The plasmid DNA of each of the groups was extracted by alkaline lysis using the QIAprep Spin Miniprep kit (Qiagen S.A., Courtaboeuf, France).

This plasmid DNA was then cotransfected, into COS-7 cells, with an HLA A*0201 vector (pHLA A*0201, obtained from T. Boon, LICR, Brussels, Belgium).

Transfection of COS-7 Cells

The COS-7 cells, cultured in DMEM (Sigma) medium containing 1 g of glucose/liter and 10% of fetal calf serum, antibiotics and L-glutamine, were transfected with the vector pHLA-A*0201, alone or in combination with the plasmid DNA derived from one of the groups of the M134 cDNA library. The transfection was carried out according to the DEAE-dextran-chloroquine protocol (Brichard, Exp. Med. 1993, 1(78): 489-495). 2×10⁴ COS-7 cells were transfected with 100 ng of plasmid pHLA-A*0201 and, for the cotransfection, 100 ng of plasmid DNA of the M134 library. 48 h after transfection, these COS-7 cells were used to stimulate the CTL clone M134.12 T. After 6 hours of coculture, the culture supernatants were removed and the TNF concentration thereof was determined by measuring their cytotoxicity for the WEHI 164 clone 13, as described above.

Among the groups tested, a positive group (270) was identified. 96 different plasmids of this group were tested individually for their ability to induce TNFα secretion by the CTL clone M134.12.

One of these plasmids, called pNA134-A, that induced TNFα secretion comparable to that obtained in the presence of the M1134 cell line, was selected.

Figure 2:
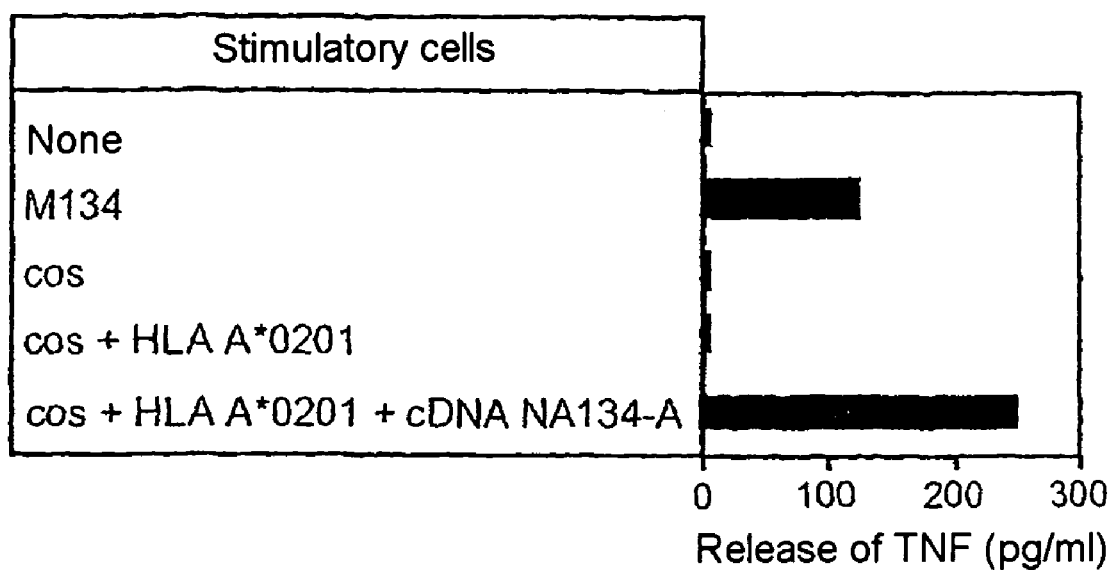
FIG. 2 compares TNF-α secretion by CTL clone M134.12 in the absence of stimulatory cells and in the presence of various types of cells.

FIG. 2 compares the TNFα secretion by the CTL clone M134.12, in the absence of stimulatory cells, in the presence of M134 cells, in the presence of nontransfected COS-7 cells, in the presence of COS-7 cells transfected with the plasmid pHLA-A*0201 alone, and in the presence of COS-7 cells cotransfected with the plasmids pHLA-A*0201 and pNA134-A.

The sequencing of pNA134-A shows that it contains in 1.3 kb cDNA, the sequence of which corresponds to the 3' end of the sequence encoding the MMP-2 metalloprotease (accession number: NM_004530). The MMP-2 protein is therefore the antigen recognized by the CTL clone M134.12.

The insert of the plasmid pNA134-A encodes amino acids 501-661 of MMP-2.

In order to specify in more detail the MMP-2 region recognized by the CTL clone M134.12, plasmids containing truncated variants of the NA134-A cDNA insert (fragment 20 encoding amino acids 501-661 of MMP-2, and fragment 25 encoding amino acids 501-556 of MMP-2) were constructed.

A plasmid comprising the entire MMP-2 cDNA was also constructed.

Each of these plasmids was cotransfected with pHLA A*0201 into COS-7 cells, which were then tested for their ability to induce TNFα secretion by the CTL clone M134.12.

Figure 3:
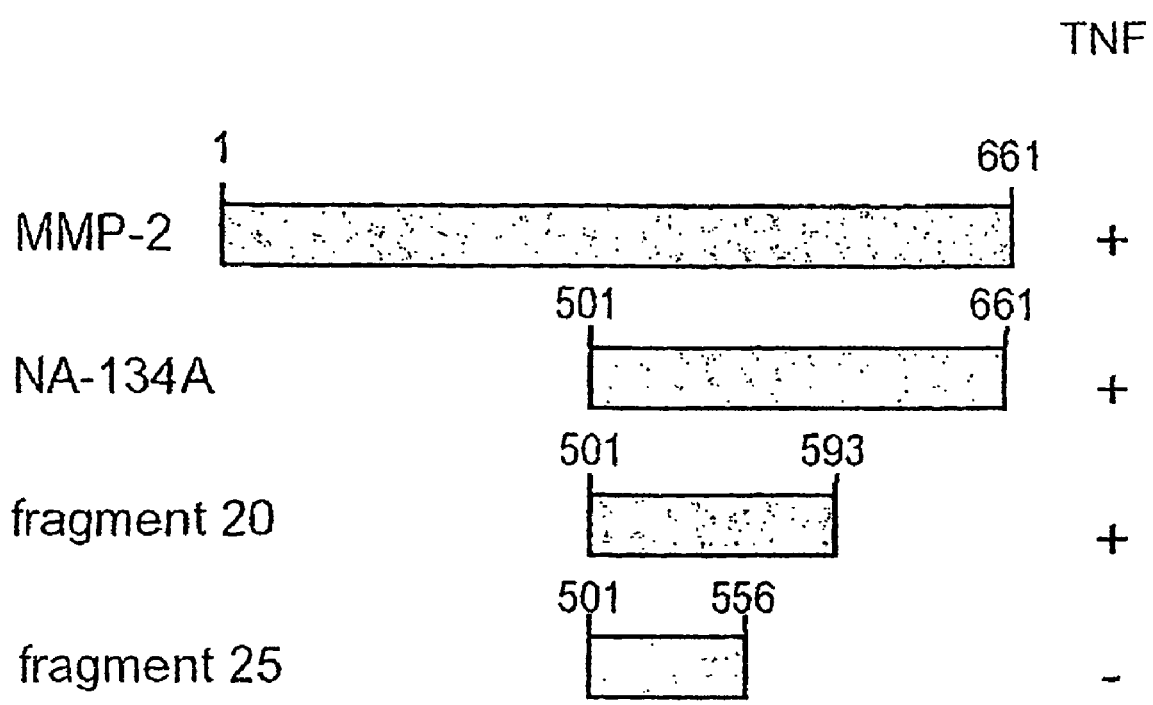
FIG. 3 depicts the ability of different plasmid constructs to induce TNF-α secretion.

The constructs tested are shown diagrammatically in FIG. 3, which also indicates their ability or non-ability to induce TNFα secretion by the CTL clone M134.12.

These results show that the T epitope recognized by the CTL clone M134.12 is located between amino acids 556 and 593 of MMP-2.

A series of peptides (sequences GLPPDVQRV (SEQ ID NO: 1), LGLPPDVQRV (SEQ ID NO: 2), LPPDVQRV (SEQ ID NO: 3) and GLPPDVQR (SEQ ID NO: 4)) derived from region 556-593 of the MMP-2 protein was synthesized (Synt: em Nîmes, France).

These peptides were used to sensitize T2 cells labeled with ⁵¹Cr. These cells were incubated for 60 minutes at 37° C. with various concentrations of each of the peptides to be tested. CTL M134.12 effector cells were then added at an effector cell/target cell ratio of 10/1. The amount of ⁵¹Cr released into the supernatant is measured 4 hours later.

Figure 4:
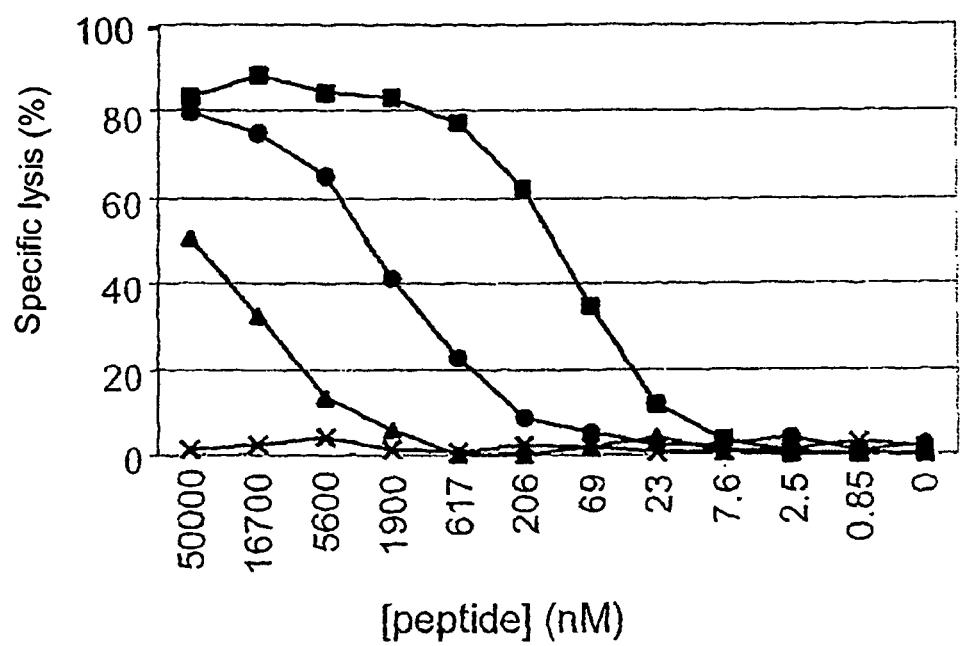
FIG. 4 shows the percentage specific lysis for various peptides over a range of peptide concentrations.

The results are illustrated in FIG. 4.

Along the y-axis, the percentage specific lysis.

Along the x-axis, the concentration of peptide LGLPPDVQRV (●) (SEQ ID NO: 2), GLPPDVQRV (■) (SEQ ID NO: 1), LPPDVQRV (▲) (SEQ ID NO: 3), or GLPPDVQR (X) (SEQ ID NO: 4) in nM.

These results show that the peptide GLPPDVQRV (SEQ ID NO: 1) is the most effective for sensitizing T2 cells to lysis by the CTL clone M134.12.

EXAMPLE 3

Expression of MMP-2 in Various Cell Types, and Specific recognition of melanoma cells by M134.12 CTLs It is known that MMP-2 is expressed constitutively by tissues such as the endometrium, the liver or the aorta (Khasigov, Biochemistry, 2001), and by a large number of cell types such as macrophages, trophoblasts (Yamamoto, Cancer Res., 1996), IL-2-activated T lymphocytes (Leppert, J I, 1995 Esparza J., Blood, 1999), fibroblasts, keratinocytes, chondrocytes, endothelial cells, monocytes or osteoblasts (Birkedal-Hansen, Crit. Rev. Oral. Biol. Med., 1993).

The ability of the CTL clone M134.12 to recognize cells (tumor cells or normal cells) of various types, expressing MMP-2 (expression verified by RT-PCR and immunohistochemistry) and HLA-A2, was tested by measuring the TNFα secretion by the CTL clone M134.12 in response to the stimulation with these cells. The protocol used is identical to that described in Example 1 above.

The results obtained are given in Table I below.

TABLE I

| | Cell type | Target cells | Recognition by the CTL clone M134.12 |
|---|---|---|---|
| Tumor lines | Melanoma | M17 | + |
| | | M113 | + |
| | | M134 | + |
| | | M147 | + |
| | | M153 | + |
| | | M204 | + |
| | | FM25 | + |
| | | FM29 | + |
| | | IPC 277/5 | + |
| | | GMEL | − |
| | | M88 | − |
| | | M117 | − |
| | Colorectal cancer | Sw480 | − |
| | Kidney carcinoma | A498 | − |
| | | R28 | − |
| | Ovary | OVCAR | − |
| | Thyroid | TT | − |

TABLE I-continued

| | Cell type | Target cells | Recognition by the CTL clone M134.12 |
|---|---|---|---|
| Normal lines | Melanocytes | 98M09 | − |
| | | 01MO08 | − |
| | Keratinocytes | K1 | − |
| | Fibroblasts | MG | − |
| | | HFFF2 | − |
| | Endothelium | HAEC#8186 | − |

These results show that 10 of the melanoma cell lines that express MMP-2 are recognized by the CTL clone M134.12. On the other hand, although they express MMP-2 and HLA-A2, none of the other cancer cell lines and no non-cancer cell line, is recognized by the CTL clone M134.12.

In conclusion, despite the ubiquitous expression profile of the MMP-2 protein, only melanoma cells appear to have the ability to effectively present an epitope of this protein.

The invention claimed is:

1. An isolated peptide consisting of the amino acid sequence of SEQ ID NO: 1.

2. A chimeric polypeptide comprising consisting of more than one copy of the isolated peptide of claim 1.

3. A composition comprising the isolated peptide of claim 1 in combination with an adjuvant.

* * * * *